United States Patent
Chen et al.

(10) Patent No.: US 9,000,775 B2
(45) Date of Patent: Apr. 7, 2015

(54) FILL-LEVEL MEASURING DEVICE FOR ASCERTAINING AND MONITORING FILL LEVEL OF A MEDIUM LOCATED IN THE PROCESS SPACE OF A CONTAINER BY MEANS OF A MICROWAVE TRAVEL TIME MEASURING METHOD

(75) Inventors: Qi Chen, Maulburg (DE); Eric Bergmann, Steinen (DE); Klaus Feisst, Stegen (DE)

(73) Assignee: Endress + Hauser GmbH + Co. KG, Maulburg (DE)

(*) Notice: Subject to any disclaimer, the term of this patent is extended or adjusted under 35 U.S.C. 154(b) by 142 days.

(21) Appl. No.: 13/809,457

(22) PCT Filed: Jul. 1, 2011

(86) PCT No.: PCT/EP2011/061088
§ 371 (c)(1),
(2), (4) Date: Jan. 10, 2013

(87) PCT Pub. No.: WO2012/007294
PCT Pub. Date: Jan. 19, 2012

(65) Prior Publication Data
US 2013/0113500 A1  May 9, 2013

(30) Foreign Application Priority Data
Jul. 13, 2010 (DE) .......................... 10 2010 031 276

(51) Int. Cl.
*G01R 27/32* (2006.01)
*G01F 23/284* (2006.01)
(Continued)

(52) U.S. Cl.
CPC .............. *G01F 23/284* (2013.01); *G01R 27/32* (2013.01); *G01N 22/00* (2013.01); *G01S 7/03* (2013.01); *G01S 13/88* (2013.01); *H01Q 1/225* (2013.01); *H01Q 13/02* (2013.01); *H01Q 19/08* (2013.01)

(58) Field of Classification Search
CPC ... G01F 23/284; G01F 23/2962; G01F 23/28; G01F 23/00; G01F 23/0061; G01F 23/14; G01F 23/263; G01F 23/296; G01F 23/2967; G01F 25/0061; G01S 7/527; G01D 11/24; G01D 21/02; G01D 5/54
USPC ................................ 324/76.56, 629, 637, 642
See application file for complete search history.

(56) References Cited

U.S. PATENT DOCUMENTS 3,114,123 A   12/1963   Kreuchen
5,262,743 A * 11/1993   Jean ............................. 333/252
(Continued)

FOREIGN PATENT DOCUMENTS

CN   101233392 A   7/2008
DE      1003826     3/1957
(Continued)

OTHER PUBLICATIONS

International Preliminary Report on Patentability dated Jan. 15, 2013, issued in Geneva, Switzerland, in International Application No. PCT/EP2011/061088.
(Continued)

*Primary Examiner* — Patrick Assouad
*Assistant Examiner* — Sean Curtis
(74) *Attorney, Agent, or Firm* — Bacon & Thomas, PLLC

(57) ABSTRACT

A fill-level measuring device for ascertaining and monitoring fill level of a medium located in the process space of a container by means of a microwave travel time measuring method. The device comprises a measurement transmitter and an antenna unit, which is constructed at least of a hollow conductor and a radiating element A microwave transmissive, process isolating element is inserted for process isolation into the hollow conductor between the measurement transmitter and the horn shaped radiating element contacting the process space. The process isolating element is embodied as a hollow body having at least one tubular hollow body region matched to the shape of the hollow conductor, and a pointed hollow body region neighboring the hollow body region in the direction of the radiating element and having a wall thickness selected based on reflection, or lack thereof, of the microwave signals.

10 Claims, 3 Drawing Sheets

(51) Int. Cl.
*G01N 22/00* (2006.01)
*G01S 7/03* (2006.01)
*G01S 13/88* (2006.01)
*H01Q 1/22* (2006.01)
*H01Q 13/02* (2006.01)
*H01Q 19/08* (2006.01)

(56) References Cited

U.S. PATENT DOCUMENTS

| | | | |
|---|---|---|---|
| 5,420,591 A * | 5/1995 | Annee et al. | 342/188 |
| 5,504,490 A * | 4/1996 | Brendle et al. | 342/118 |
| 6,415,660 B1 * | 7/2002 | Sinz et al. | 73/290 R |
| 6,581,460 B1 * | 6/2003 | Laun | 73/290 V |
| 6,677,891 B2 * | 1/2004 | Fehrenbach et al. | 342/124 |
| 6,684,919 B2 * | 2/2004 | Gaiser | 141/95 |
| 6,806,824 B2 * | 10/2004 | Kornle et al. | 342/118 |
| 6,911,929 B2 * | 6/2005 | Laun | 341/155 |
| 6,928,866 B2 * | 8/2005 | Michalski et al. | 73/290 R |
| 7,068,213 B2 | 6/2006 | Muller | |
| 7,134,315 B1 | 11/2006 | Stigler | |
| 7,224,944 B2 * | 5/2007 | McEwan | 455/86 |
| 7,408,501 B2 * | 8/2008 | Rolfes et al. | 342/124 |
| 7,639,177 B2 * | 12/2009 | Welle et al. | 342/124 |
| 7,640,799 B2 | 1/2010 | Griessbaum | |
| 7,826,309 B2 * | 11/2010 | Spanke et al. | 367/99 |
| 7,999,725 B2 * | 8/2011 | Feisst et al. | 342/124 |
| 8,482,296 B2 * | 7/2013 | Reimelt et al. | 324/644 |
| 8,567,251 B2 * | 10/2013 | Welle et al. | 73/602 |
| 2002/0112774 A1 * | 8/2002 | Gaiser | 141/1 |
| 2002/0154052 A1 * | 10/2002 | Fehrenbach et al. | 342/124 |
| 2003/0030517 A1 | 2/2003 | Munley | |
| 2003/0146867 A1 * | 8/2003 | Kornle et al. | 342/124 |
| 2003/0167839 A1 * | 9/2003 | Burger et al. | 73/290 V |
| 2003/0168674 A1 | 9/2003 | Muller et al. | |
| 2004/0056667 A1 * | 3/2004 | Lutke et al. | 324/644 |
| 2004/0074295 A1 * | 4/2004 | Michalski et al. | 73/290 R |
| 2004/0183550 A1 * | 9/2004 | Fehrenbach et al. | 324/662 |
| 2005/0132797 A1 | 6/2005 | Klees | |
| 2005/0164643 A1 * | 7/2005 | McEwan | 455/67.15 |
| 2005/0253751 A1 * | 11/2005 | Feisst et al. | 342/124 |
| 2005/0264441 A1 * | 12/2005 | Abrahamsson | 342/124 |
| 2006/0169040 A1 * | 8/2006 | Spanke | 73/290 V |
| 2007/0101809 A1 * | 5/2007 | Roesner | 73/290 R |
| 2007/0186678 A1 * | 8/2007 | Griessbaum et al. | 73/861 |
| 2008/0129583 A1 * | 6/2008 | Larsson et al. | 342/124 |
| 2008/0143583 A1 * | 6/2008 | Welle et al. | 342/124 |
| 2008/0302439 A1 * | 12/2008 | Spanke et al. | 141/1 |
| 2008/0303710 A1 * | 12/2008 | Kienzle et al. | 342/124 |
| 2009/0178478 A1 * | 7/2009 | Reimelt et al. | 73/290 V |
| 2009/0212996 A1 * | 8/2009 | Chen et al. | 342/124 |
| 2010/0141505 A1 * | 6/2010 | Bergmann et al. | 342/124 |
| 2010/0162811 A1 * | 7/2010 | Malinovskiy et al. | 73/290 V |
| 2010/0307251 A1 * | 12/2010 | Welle et al. | 73/627 |
| 2011/0161019 A1 * | 6/2011 | Mayer | 702/55 |
| 2011/0166805 A1 * | 7/2011 | Hammer et al. | 702/55 |
| 2012/0056628 A1 * | 3/2012 | Michalski et al. | 324/629 |

FOREIGN PATENT DOCUMENTS

| | | | | |
|---|---|---|---|---|
| DE | 19641036 A1 | 4/1998 | | |
| DE | 10360711 A1 * | 7/2005 | | |
| DE | 10 2005036715 A1 | 2/2007 | | |
| DE | 102006003742 A1 | 8/2007 | | |
| DE | 102006062223 A1 * | 6/2008 | | G01F 23/284 |
| DE | 603 19930 T2 | 4/2009 | | |
| EP | 0834722 A3 | 4/1998 | | |
| EP | 1431724 A1 * | 6/2004 | | G01F 23/284 |
| WO | WO 01/88488 A1 | 11/2001 | | |

OTHER PUBLICATIONS

German Search Report, Jul. 13, 2010, Munich.
International Search Report, Oct. 31, 2011, EPO, The Netherlands.

* cited by examiner

FILL-LEVEL MEASURING DEVICE FOR ASCERTAINING AND MONITORING FILL LEVEL OF A MEDIUM LOCATED IN THE PROCESS SPACE OF A CONTAINER BY MEANS OF A MICROWAVE TRAVEL TIME MEASURING METHOD

TECHNICAL FIELD

The present invention relates to a fill-level measuring device for ascertaining and monitoring fill level of a medium located in the process space of a container by means of a microwave travel time measuring method. The device includes a measurement transmitter and an antenna unit, which is constructed at least of a hollow conductor and a radiating element, wherein a microwave transmissive, process isolating element is inserted for process isolation into the hollow conductor between the measurement transmitter and the horn shaped radiating element contacting the process space.

BACKGROUND DISCUSSION

Endress+Hauser, the assignee of the present application, works in the field of industrial automation- and process control technology and manufactures industrial measuring devices, also referred to as field devices. It sells these field devices e.g. for fill level determination of a medium in a container. Such devices include, among others, devices sold under the marks, MICROPILOT, LEVELFLEX and DELTAPILOT.

A known measuring method, among a large number of measuring methods for ascertaining fill level in a container, is the travel time, measuring method. In the case of this measuring method, for example, microwaves are transmitted via an antenna apparatus and echo waves reflected on the surface of the medium detected, wherein the travel time of the measurement signal is a measure for the distance traveled. From half the travel time, accordingly, fill level of the medium in a container can be ascertained. The echo curve represents, in such case, the total course of the signal as a function of time, wherein each measured value of the echo curve corresponds to the amplitude of an echo signal reflected on a surface located at a certain distance. The travel time, measuring method is essentially divided into two methods of ascertainment: In the case of the time-difference method, the time, which a broadband signal pulse requires for a traveled path, is ascertained. In the case of the frequency difference method (FMCW—Frequency-Modulated Continuous Wave), the transmitted, frequency modulated, high-frequency signal is compared with the reflected, received, frequency modulated, high-frequency signal. In the following, no limitation is intended as to which particular method of measurement is used.

In the case of certain process applications, the measuring devices, or their sensor elements, are exposed to extreme conditions, such as e.g. high temperatures, high pressures and/or chemically aggressive substances. Especially, microwave fill level measuring devices have temperature- and/or pressure-sensitive components, such as, for example, the measuring device electronics and transmitting- and/or receiving elements for the microwaves. Moreover, the radiating characteristics of the antennas of the microwave fill level measuring devices are changed by accretions of medium.

In order to protect the measuring electronics in the measurement transmitter and the microwave signal coupling structures against high temperatures, high pressures and aggressive chemical materials, as well as to hold the radiating characteristics of the antennas constant, sensitive elements of the sensor elements, respectively the antennas, are hermetically sealed on the process-side with process isolation elements. Moreover, by joining a hermetically sealed, process isolating element into the hollow conductor of a horn antenna, the greatest possible safety is assured, since, due to a second "safety element", the process, with an isolation of the modular measurement-active parts, such as e.g. an in-coupling unit/exciter element or the measuring device electronics, from the measurement passive parts, such as e.g. the antenna, still remains sealed, should maintenance or repair of the fill-level measuring device become necessary.

Described in WO 2003/046491 A1 is an antenna for fill level measurement, which is protected against aggressive chemical media and high temperatures by means of at least partial filling with a dielectric material or a disk or washer shaped, dielectric element.

U.S. Pat. No. 5,115,218 B2 discloses a microwaves transmissive, process isolating element, whose conical formation uses Brewster's angle, which is the angle for total transmission of the radiation energy through a dielectric medium.

Shown in WO 2000/29819 A1 is a microwaves process isolation window for a bypass-pipe that has a conical formation and is hermetically sealed via O-rings between process connection nozzle on the container and device connection nozzle.

Presented in DE 10 2007 026 389 A1 is a high temperature process isolation, which has an attenuating, or damping, element, which improves measurements in the vicinity of the antenna by reducing ringing.

Disadvantageous in the case of the process isolation elements shown in the state of the art is that the synthetic materials of the process isolating element and the seal elastomers are not durable in the temperature range >200° C. and, with rising temperature, very rapidly age- and, as a result thereof, have leakage problems.

SUMMARY OF THE INVENTION

An object of the invention, therefore, is to provide a reflection poor and resonance free, process separating element for a fill-level measuring device, wherein the process separating element has a high thermal and chemical durability and is especially cost effectively and easily manufactured.

The object is achieved by a fill-level measuring device of the invention for ascertaining and monitoring fill level of a medium located in the process space of a container by means of a microwave travel time measuring method which includes a measurement transmitter and an antenna unit, which is constructed at least of a hollow conductor and a radiating element, wherein a microwave transmissive, process isolating element is inserted for process isolation into the hollow conductor between the measurement transmitter and the horn shaped radiating element contacting the process space.

According to the invention, the process isolating element is embodied as a dielectric hollow body having at least one tubular hollow body region matched to the shape of the hollow conductor, and a joining, pointed hollow body region neighboring the tubular hollow body region in the direction of the radiating element and having a wall thickness selected based on reflection, or lack thereof, of the microwave signals.

In a first embodiment, the selected wall thickness of the process isolating element, especially in the pointed hollow body region, lies steadily at about half the wavelength of the transmitted microwave signal or at a whole number multiple thereof.

In a second embodiment, the selected wall thickness of the process isolating element, especially in the pointed hollow body region, lies in a range of one to five millimeters.

In the first or second embodiment, the tubular hollow body region of the process isolating element is embodied as a circular cylinder and the pointed hollow body region of the process isolating element has a conical formation toward the process space.

In the first or second embodiment, the tubular hollow body region of the process isolating element is embodied as a rectangular cylinder and the pointed hollow body region of the process isolating element has a wedge shaped or pyramid shaped formation toward the process space.

In an advantageous embodiment, there is present in the tubular hollow body region of the process isolating element up to the pointed hollow body region a metal tube electrically connected with the metal hollow conductor or, electrically connected with the metal hollow conductor, a metal coating of the inner wall of the tubular hollow body region of the process isolating element.

In an especially advantageous embodiment, the pointed hollow body region has a defined acute angle, wherein half the acute angle corresponds to ninety degrees, or a right angle, minus Brewster's angle, of the microwave signals falling on the area of the pointed hollow body region.

In a supplemental embodiment, the process isolating element has toward the hollow conductor a collar region on the tubular hollow body region, whereby a sealed clamped securement of the collar region of the process isolating element to the hollow conductor is effected by means of a screwed and/or welded, nozzle element.

In an additional embodiment, the process isolating element seals by means of at least one seal, especially an O-ring-seal, graphite compression gland-seal, or a ceramic-metal-soldered connection, which seals the hollow conductor hermetically.

In order to suppress possibly occurring, high frequency-resonances in the dielectric body and to improve the radiating characteristics of the antenna unit, an absorber element of a high frequency-attenuating material, especially a silicon carbide washer, is present in the joint of the hollow conductor with the process isolating element.

In an embodiment facilitating the object of the invention, the process isolating element comprises a ceramic material, a synthetic material, a dielectric composite material, such as e.g. a fiber reinforced, synthetic material, a ceramic filled synthetic material or a glass. Ceramic material optimized for technical applications is, due to its high pressure resistance, especially suitable for this type of construction.

BRIEF DESCRIPTION OF THE DRAWINGS

Further details, features and advantages of the subject matter of the invention will become evident from the following description with the associated drawing, in which preferred examples of embodiments of the invention are presented. Components or assemblies of components of the examples of embodiments illustrated in the figures corresponding in their construction and/or in their function are, for better overview and for simplification, provided with equal reference characters. The figures of the drawing show as follows.

DETAILED DISCUSSION IN CONJUNCTION WITH THE DRAWINGS

Figure 1:
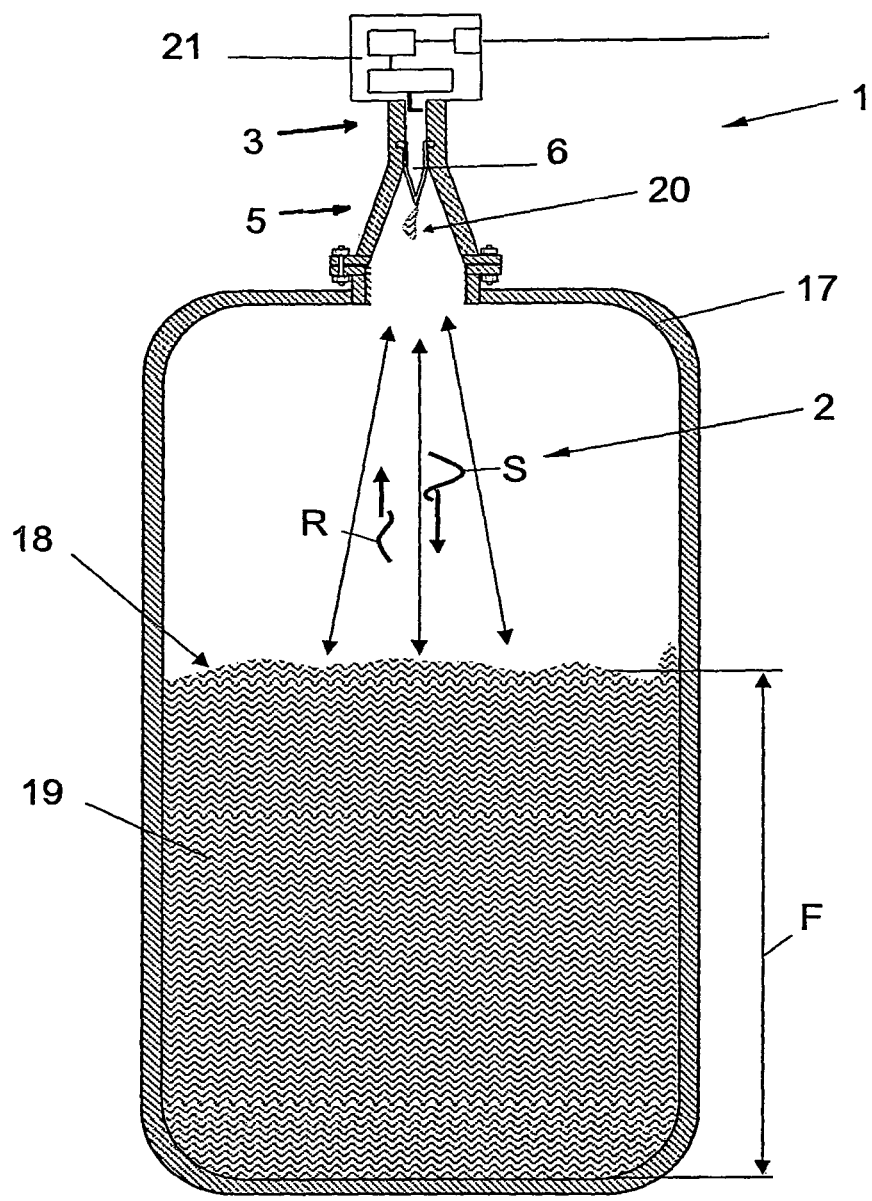
FIG. 1 is a schematic sectional illustration of a fill-level measuring device of process measurements technology, with a horn antenna and the process isolating element of the invention.

FIG. 1 shows a fill-level measuring device 1 working according to the travel time, measuring method for ascertaining fill level F of a medium 19. As shown, fill-level measuring device 1 is mounted on a nozzle of a container 17. The illustrated fill-level measuring device 1 is composed of a radiating element 5, especially a horn antenna, radiating microwaves freely into the process space and a measurement transmitter 21. Measurement transmitter 21 includes at least one transmitting/receiving unit, which produces the transmission signals T and receives the reflection signals R of the microwave signals 2, a control/evaluation unit, which cares for signal processing of the microwave signals 2 and for control of the fill-level measuring device 1, and, moreover, a communication unit, which controls communication via a bus system as well as the energy supply of the fill-level measuring device 1. The radiating element 5 is embodied in this example of an embodiment, for example, as a horn antenna. However, the radiating element 5 can be any known antenna, such as e.g. a rod antenna or a planar antenna. In the transmitting/receiving unit, a microwave signal 2 is produced, for example, in the form of transmission signal T, and radiated via the antenna unit 3 with a predetermined radiation characteristic in the direction of the medium 19. After a travel time t dependent on the traveled distance x, the transmission signals T, reflected on the bounding surface 18 of the medium 19 as reflection signal R, are received back by the antenna unit 3 and the transmitting/receiving unit. The control/evaluation unit then ascertains from the reflection signals R an echo curve 22, which shows amplitude Amp of the reflection signals R as a function of the traveled distance x or the corresponding travel time t. An analog/digital conversion of the analog echo curve 22 then leads to a digitized, envelope curve.

The process isolation and sealing of an antenna unit 3 by means of an process isolating element 6 of the invention, as shown in FIGS. 1-5, is crucial for the practical use of the fill-level measuring device 1 in the process, since the process isolating element 6 of the invention protects the antenna unit 3 from chemically aggressive media and prevents the influencing of the radiating characteristic of the antenna unit due to accretion 20 of the medium 19. In fill level measuring technology, especially great technical requirements are placed on the process isolation of a radar-antenna unit 3, since the working conditions as regards pressure, temperature, and durability against process media 19 can be quite different.

The microwave signals 2 should be transmitted through the process isolating element 6 of the invention with as little reflection, and as resonance freely, as possible, so that only dielectric materials can be considered for building the process isolating element 6. The process isolating element 6 should, among others things, have the following properties as regards material:

high temperature resistance,
high chemical durability,
resistant against steam,
high pressure resistance, good sealing properties with little diffusion of the medium through the material, and good condensate drop shedding behavior and lack of susceptibility to accretion and condensate accumulation.

The process isolating element 6 of the fill-level measuring devices 1, which ascertain the distance to the medium 19 using a travel time measuring method with microwave signals 2, is usually arranged between the in-coupling of the coaxial signal guidance into the hollow conductor 4 of the antenna unit 3 and the radiating element 5, e.g. a horn antenna. The process isolating element 6 should avoid that medium 19 can penetrate from the process into the sensitive coupling structure and the measurement transmitter 21 and/or escape into the environment.

The process isolating element 6 according to the state of the art for horn antennas is a hollow conductor filled with a dielectric, such as, for example, shown in U.S. Pat. No. 3,594,667 B1, wherein the fill material conically tapers at the location where the horn of the horn antenna begins to widen. Applied as dielectric materials are, most often, polymer materials, especially PTFE (polytetrafluoroethylene) or PEEK (polyether ether ketone). The process insolating elements 6 of the invention, being made of these polymer synthetic materials, are inserted in combination with the elastomer seal hermetically sealingly into the hollow conductor 4. The diameter of the process isolating element 6 in the region of the hollow conductor 4 is so selected that only the fundamental mode of the microwave signals 2 is capable of propagation in the filled hollow conductor 4 at the maximum working frequency and, thus, no disturbing resonances of higher modes arise in the hollow conductor 4. The process insolating elements 6 of synthetic material have the advantage that they are very inexpensive and easy to manufacture. The disadvantages lie in the limited service temperature of maximum 200° C. of these applied synthetic materials, especially the elastomeric sealing materials, and in the limited pressure resistance resulting from the low strength and from the flow characteristics of the polymer material, especially PTFE (polytetrafluoroethylene).

Above this service temperature of 200° C., exclusively ceramic remains as dielectric material, since glasses for technical applications in the case of these increased temperatures of via 200° C. are not resistant to water and steam. These ceramic materials have, most often, a high temperature- and/or chemical durability, as well as higher pressure resistance. The disadvantages of these ceramic materials for application as process isolating element 6 lie in the brittleness and higher dielectric constant than in the case of synthetic materials. The ceramic materials have dielectric constants greater than 2. The high dielectric constant leads to the fact that, at significantly smaller diameter and relatively high working frequency, especially over 20 GHz, the fraction of the microwave signals reflected back by the process isolating element 6 into the hollow conductor 4 is strongly increased and this can lead to production of disturbance signals coming from high frequency resonances of the higher modes of the microwave signal 2. This reinforced reflection of the microwave signal 2 on the process isolating element 6 due to the higher dielectric constant of the material has furthermore the disadvantage that less energy is radiated as transmission signal T into the process space, respectively into the container 17. Moreover, the higher dielectric constant also significantly lessens the ability of the antenna unit to function reliably in the face of condensate. For example, the diameter of the process isolating element 6 of an aluminum oxide ceramic with a monomodal propagation characteristic of the microwave signal 2 in the case of 26 GHz amounts to about 2.7 mm. These small diameters of the process insolating element 6 at these high excitation frequencies are only manufacturable with great technical effort and high costs. A possibility for avoiding this problem is to make the diameter of the process isolating element 6 larger, thus design multimodally. This larger dimensioned, multimode process isolating element 6 in a hollow conductor 4 causes the formation of higher modes in the hollow conductor 4 due to high frequency resonances. These high frequency resonances are referred to in the technical literature also as high frequency "ringing" and can mask the echo of the fill level in certain measuring ranges, whereby the evaluation of the travel time of the echo pulses is no longer possible and the dynamics of the fill-level measuring device 1 are reduced. In DE 10 2007 026 389 A1, a structural improvement of the antenna unit 3 for suppressing the high frequency resonances, or "ringing", is described, wherein the "ringing" is damped, or attenuated, with the absorber 11. The absorber 11, on the other hand, brings about a smaller antenna reinforcement, or amplification, and multimodal radiation into the process space by higher modes must be tolerated with this construction.

The high temperature antenna of the invention in FIGS. 1-5 has an alternative construction, which includes a process isolating element 6 of a dielectric, thin walled, hollow body 7. The wall thickness d of the process isolating element 6 amounts to about $\lambda/2$ or a multiple thereof, at least in the pointed hollow body region 9, wherein $\lambda$ corresponds to the average wavelength of the broadband excited, microwave signal 2. If the microwave signal 2 is fed in via a round, air-filled, hollow conductor 4 into the hollow body region 8, the pointed hollow body region 9 is embodied as a hollow cone. If, in contrast, the microwave signal 2 is fed in via a rectangular, air-filled, hollow conductor 4 into the hollow body region 8, then the pointed hollow body region 9 is embodied as a hollow pyramid. The quasi linearly polarized TE-11 mode leaves the, for example, round, hollow conductor 4, passes through the pointed hollow body region 9 formed as a hollow cone and having a wall thickness d of $\lambda/2$ or a multiple thereof, and is then radiated via the radiating element 5, which is a horn in FIGS. 1-5. The conical construction increases the HF bandwidth and the measuring dynamic of the antenna unit 3 and improves simultaneously the condensate insensitivity in comparison to planar, hollow conductor windows and a hollow conductor 4 filled completely with a dielectric.

Depending on how the antenna unit 3 is constructed, a large hollow body 4 can form in the tubular hollow conductor region 8, in which, in turn, high frequency resonances of higher modes of the microwave signal 2 can arise. In order that these resonance signals do not disturb the detection of the echoes of the transmission signals T, an absorber 11 is added for damping, or attenuating, the resonance signals. Because of the desired pressure resistance of the process isolating element 6 with a pointed hollow body region 9, whose wall thickness d equals half the average wavelength of the microwave signal, i.e. $\lambda/2$ or a multiple thereof, this hollow body 7—construction of the process isolating element 6 of the invention is limited to the frequency range of less than 40 GHz, since otherwise the resistance of the process isolating element 6 to high pressures of up to some hundred bar can no longer be assured.

Figure 2:
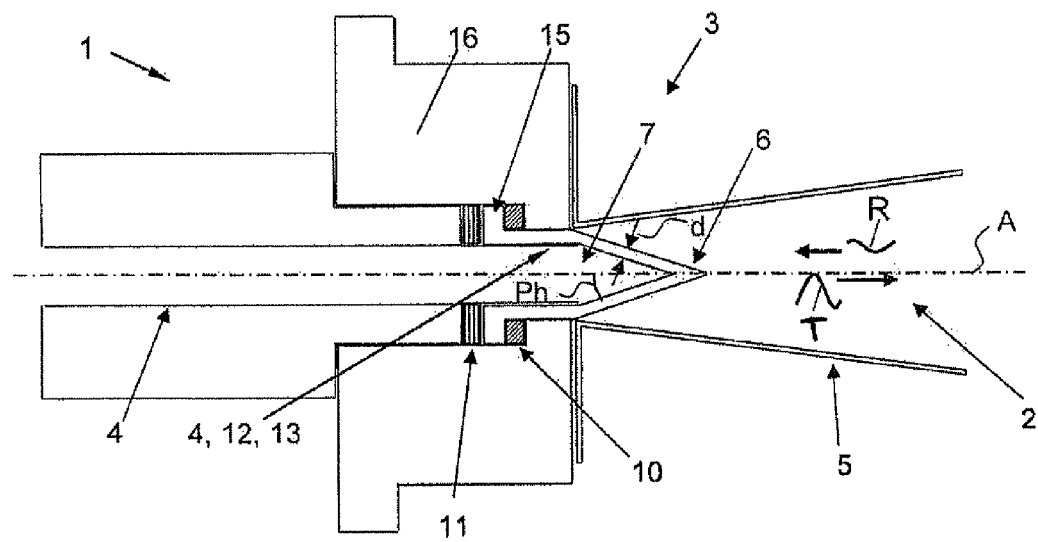
FIG. 2 is a sectional illustration of an example of an embodiment of the process isolating element of the invention.

FIG. 2 shows the process isolating element 6 of the invention in an antenna unit 3. Antenna unit 3 is composed at least of a hollow conductor 4, which is so mounted in a process connection, respectively in a nozzle element, 16 that the process isolating element 6 of the invention is hermetically sealed in the collar region 15 by means of a seal 10 and held in place by shape-interlocking. For this, for example, a screw thread is formed in the outer wall of the hollow conductor 4, which is screwed into a screw thread in the inner wall of the process connection 16, so that, via the inserted seal 10, a clamped securement of the process isolating element 6 occurs in the collar region 15. Inserted as seal is here, for example, a metal sealing washer. The screwed, clamped connection is, in the mounted state, hermetically sealingly secured and held against unscrewing, for example, supplementally by a welding of the process connection 16 with the hollow conductor 4 at their exposed joint. Additionally, for attenuation or damping of undesired, potentially arising, high frequency resonances, an absorber 11 in the form a silicon carbide washer is inserted in the joint between the end of the hollow conductor 4 and the collar region 15 of the process isolating element 6. For improving the radiation characteristic, respectively for improving the planar wavefront of the microwave signal 2, a horn antenna as radiating element 5 is so placed on the process connection 16 in the direction of radiation that the antenna horn begins to widen at the location where the pointed hollow body region 9 begins, respectively where the diameter of the hollow cone, or the hollow pyramid, begins its tapering narrower. The hollow conductor 4 is, for example, either further extended via a thin, tubular element into the hollow body region 8 of the hollow body 7 of the process isolating element 6, or the inner wall 13 of the hollow body 7 of the process isolating element 6 of the invention is provided in the hollow body region 8 with a metal, closed or partially open, coating 12, which is electrically connected with the rest of hollow conductor 4. Through this extension of the hollow conductor 4 into the rectangular or cylindrical hollow body region 8, on the one hand, a further mechanical reinforcement of the construction of the process isolating element 6 can be achieved, while, on the other hand, disturbance reflections in the hollow body region 8 of the process isolating element 6 due to diameter-changes of the hollow conductor structure 4 are prevented.

Figure 3:
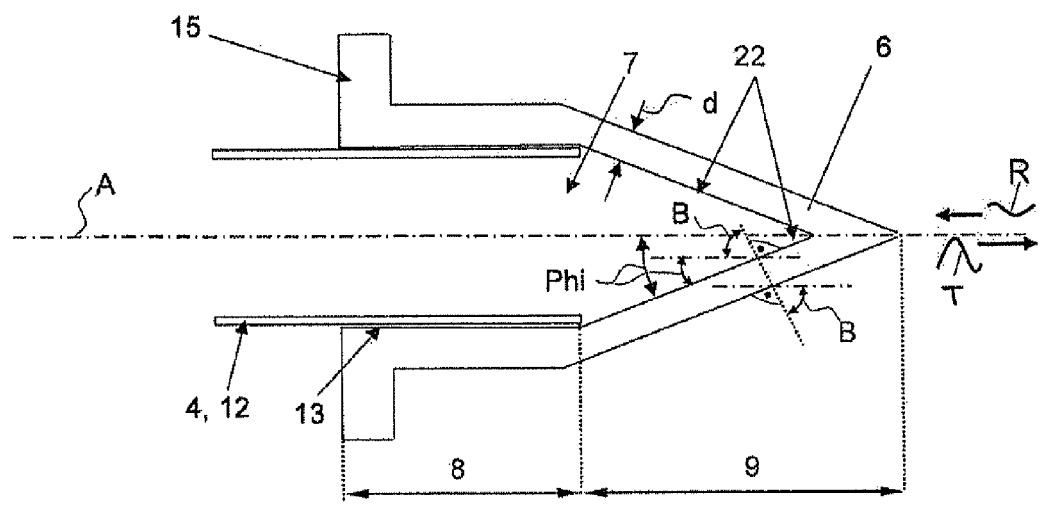
FIG. 3 is an enlarged representation of the process isolating element of the invention for the fill-level measuring device of process measurements technology of FIG. 2.

FIG. 3 shows an enlarged partial view of FIG. 2, limited to the process isolating element 6 and the extension of the hollow conductor 4 into the hollow body 7. The process isolating element 6 of the invention is embodied as hollow body 7 and includes a collar region 15 with thereon following, hollow body region 8 and pointed body region 9. The metal hollow conductor 4 is extended into the entire length of the hollow body region 8, or a metal coating 12 of the inner wall 13 in the hollow body region 8 results in a hollow conductor 4 in this hollow body region 8. The process isolating element 6 is, in the case of a circularly round, hollow conductor 4, constructed of at least one circular cylinder in the hollow body region 8 with an adjoining, circularly symmetric pointed hollow cone in the pointed hollow body region 9. The process isolating element 6 is, thus, rotationally symmetrically embodied about an axis A. Another embodiment results in the case of the application of a rectangular hollow conductor 4 in the antenna unit 3, which is embodied of at least one rectangular cylinder in the hollow body region 8 and a thereto adjoining, hollow pyramid in the pointed hollow body region 9. In a supplemental embodiment, which is not shown explicitly in the figures, the pointed hollow cone or the hollow pyramid is broken down into a planar region, so that corresponding Fresnel structures result. Pointed body region 9 has a wall thickness d amounting to about half the average wavelength $\lambda/2$ of the transmitted microwave signals 2 or a multiple thereof. The acute angle Phi of the sides 22 of the hollow body 7 in the pointed hollow body region 9 relative to an axis A pointing in the radiating direction of the microwave signals 2 is equal to a right angle, or the angle of the surface normals to the sides 22 minus the Brewster's angle B of the transmission signals T and/or reflection signals R of the microwave beams. The microwave signals 2, which impinge on the sides 22 of the hollow body 7 in the pointed hollow body region 9 on the bounding surface between the air-filled hollow conductor 4 and the dielectric material of the process isolating element 6 with different indices of refraction, are reflected, respectively transmitted through the material of the process isolating element 6, according to the Fresnel equations. In the Fresnel equations, reflection depends both on the angle of incidence, respectively Brewster's angle B, and the indices of refraction of the materials, as well as on the polarization of the incoming light. For the microwave signal, respectively microwave radiation, 2 with a polarization parallel to the incident plane and incident with the Brewster's angle B, the reflection of the microwave signal 2 is completely canceled and the microwave signals 2 are transmitted completely through the surface and the material of the process isolating element.

Figure 4:
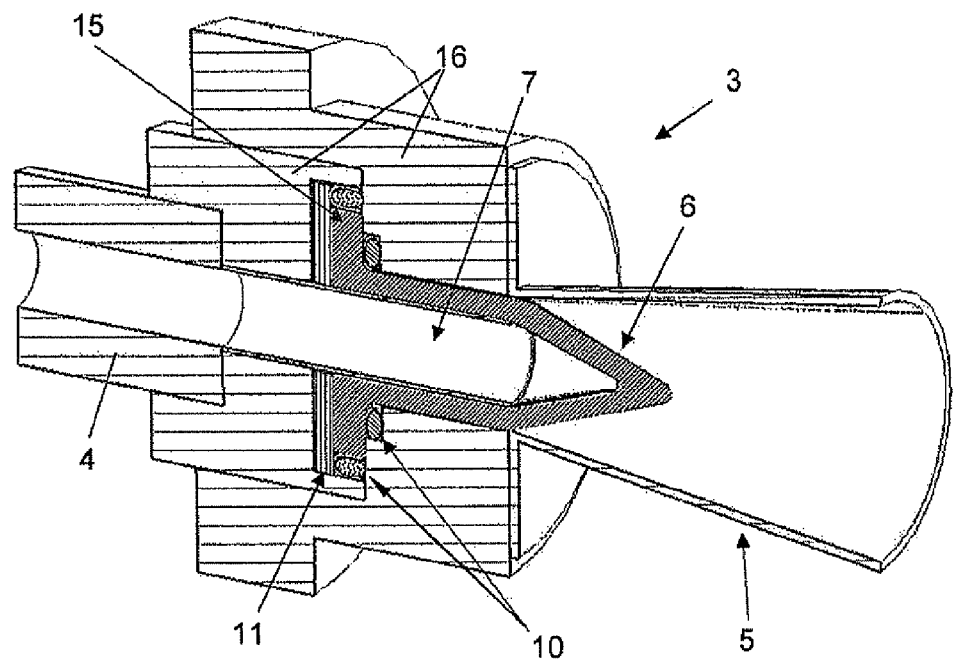
FIG. 4 is a three-dimensional sectional illustration of the process isolating element of the invention.

FIG. 4 shows a three-dimensional, longitudinal section of the antenna unit 3 of the invention. The process isolating element 6 of the invention of FIGS. 1 to 3 is placed in this embodiment between a first and a second part of a multi-part process connection, or nozzle element, 16. Mounted on the process connection 16 in the radiating direction is an antenna horn as radiating element 5 for adapting the radiation characteristic of the microwave signals 2 freely radiating into the process space. The first and second parts of the multi-part embodied, process connection, or nozzle element, 16 are, in such case, for example, so screwed into one another via screw threading that they mechanically clamp the process isolating element 6 in the collar region 15. Inserted in the collar region for hermetic sealing of the process isolating element are two sealing elements, e.g. metal O-rings, which are compressed by the clamped connection between the process connection 16 and the process isolating element 6 for sealing. For absorption of possible disturbance modes due to high frequency resonances, an absorber 11 is integrated into the clamped connection. The hollow conductor 4 is extended into the process isolating element up to the pointed hollow body region, so that the microwave signals 2 can propagate in an undisturbed hollow conductor 4 up to the pointed hollow body region 9 in the case of a circularly cylindrical, hollow conductor 4 in the undisturbed, quasi linear, polarized TE11 mode. By embodying the sides 22 of the pointed hollow body region 9 relative to the propagation axis A of the microwave signals 2 with a Brewster's angle Phi and with a wall thickness d of half the average wavelength $\lambda/2$ of the microwave signals 2, almost the entire part of the microwave signal 2 to be transmitted is transmitted and, in given cases, only a small part reflected back into the hollow conductor 4 as disturbing resonance.

Figure 5:
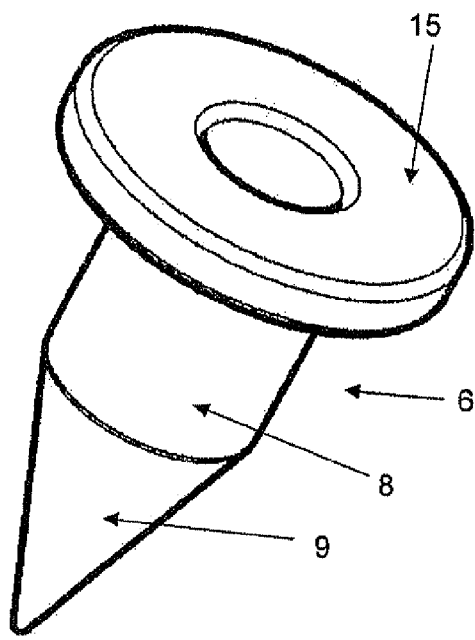
FIG. 5 is a perspective view of the process isolating element of the invention.

FIG. 5 shows a complete view of the process isolating element 6 of the invention with a collar region 15 in the form of a circular washer, the hollow body region 8 in the form of a circular cylinder and the pointed hollow body region 9 in the form of a hollow cone. Elements like this can be manufactured, for example, in known, ceramic casting methods or compacting press methods, for example compacting press methods utilizing embossing techniques, and, thus, are cost effectively and easily manufacturable.

For example, the process isolating element 6 shown in FIGS. 4-5 has, at a center frequency of the microwave signals 2 of 26 GHz in the case of an aluminum oxide ceramic material, an outer diameter of 13 millimeters and an inner diameter of about 9 millimeters. The process isolating element of the invention is so designed that it can directly withstand process conditions including temperatures in the range T=−270 to 450° C. and a pressures in the range p=−1 to 160 bar. In order to be able to assure gas tightness of the total antenna unit 3, the ceramic body of the process isolating element 6 is sealed primarily with a metal O-ring and, secondarily, installed using a metal ceramic soldered connection. The attenuating material of the absorber 11 is, for example, a washer of a silicon carbide ceramic applied in the collar region 15 of the process isolating element 6.

If, in comparison, the process isolating element 6 is embodied according to the state of the art as a completely filled, monomodal, hollow conductor, isolating element, the required outer diameter in the cylindrical region of the process isolating element 6, in the case of application of an aluminum oxide ceramic and a frequency of the microwave signals 2 of 26 GHz, amounts, for example, to about 2.7 mm. These specifications only lead to increased cost and lessening of the accuracy of measurement.

The invention claimed is:

1. A fill-level measuring device for ascertaining and monitoring fill level of a medium located in the process space of a container by means of a microwave travel time measuring method, such device comprising:
a measurement transmitter;
an antenna unit, which is constructed at least of a hollow conductor and a horn shaped radiating element; and
a microwave transmissive, process isolating element inserted for process isolation into said hollow conductor between said measurement transmitter and
said horn shaped radiating element contacting the process space, wherein:
said process isolating element is embodied as a hollow body having at least one tubular hollow body region matched to the shape of said hollow conductor, and a pointed hollow body region neighboring said tubular hollow body region in the direction of said radiating element and having a wall thickness selected based on reflection, or lack thereof, of the microwave signals, and
there is present in said tubular hollow body region of said process isolating element up to said pointed hollow body region a metal tube electrically connected with said hollow conductor or, electrically connected with said hollow conductor, a metal coating of the inner wall of said tubular hollow body region of said process isolating element.

2. The device as claimed in claim 1, wherein:
the selected wall thickness of said process isolating element, especially in said pointed hollow body region, lies steadily at about half the wavelength of the transmitted microwave signal or at a whole number multiple thereof.

3. The device as claimed in claim 1, wherein:
the selected wall thickness of said process isolating element, especially in said pointed hollow body region, lies in a range of one to five millimeters.

4. The device as claimed in claim 1, wherein:
said tubular hollow body region of said process isolating element is embodied as a circular cylinder and said pointed hollow body region of said process isolating element has a conical formation toward the process space.

5. The device as claimed in claim 1, wherein:
said tubular hollow body region of said process isolating element is embodied as a rectangular cylinder and said pointed hollow body region of said process isolating element has a wedge shaped or pyramid shaped formation toward the process space.

6. The device as claimed in claim 1, wherein:
said pointed hollow body region has an acute angle, wherein half the acute angle corresponds to ninety degrees minus Brewster's angle.

7. The device as claimed in claim 1, wherein:
said process isolating element has toward said hollow conductor a collar region on said tubular hollow body region, whereby a sealed clamped securement of said collar region of said process isolating element to said hollow conductor is effected by means of a screwed and/or welded nozzle element.

8. The device as claimed in claim 1, wherein:
said process isolating element seals by means of at least one seal, especially an O-ring-seal, graphite compression gland-seal, or a ceramic-metal-soldered connection, which seals said hollow conductor hermetically.

9. The apparatus as claimed in claim 1, wherein:
an absorber element, especially a silicon carbide washer, is present in the joint of said hollow conductor with said process isolating element.

10. The apparatus as claimed in claim 1, wherein:
said process isolating element comprises a ceramic material, a synthetic material, a dielectric composite material, such as e.g. a fiber reinforced, synthetic material, a ceramic filled synthetic material or a glass.

* * * * *